United States Patent
Bruns et al.

[11] Patent Number: 5,842,863
[45] Date of Patent: Dec. 1, 1998

[54] DEVICE FOR CONTAINING EXCESS ABRASIVE MATERIAL

[76] Inventors: Craig C. Bruns, 10 Montecito Dr.; Mark S. Fernwood, 450 Montcrest Dr., both of Danville, Calif. 94526

[21] Appl. No.: 909,681

[22] Filed: Aug. 12, 1997

[51] Int. Cl.$^6$ ................................................. A61C 1/16
[52] U.S. Cl. ............................................ 433/116; 433/88
[58] Field of Search ............................. 433/116, 80, 125, 433/166, 88, 86, 91; 408/67; 604/198; 606/180; 451/453, 455, 456

[56] References Cited

U.S. PATENT DOCUMENTS

| | | | |
|---|---|---|---|
| 4,286,950 | 9/1981 | Hawk | 433/116 |
| 4,611,992 | 9/1986 | Lokken | 433/116 |
| 4,850,868 | 7/1989 | Wright et al. | 433/116 |
| 5,122,153 | 6/1992 | Harrel | 606/180 |
| 5,197,876 | 3/1993 | Coston . | |
| 5,199,229 | 4/1993 | Herold et al. . | |
| 5,356,292 | 10/1994 | Ho | 433/116 |
| 5,547,376 | 8/1996 | Harrel | 433/116 |

*Primary Examiner*—Gene Mancene
*Assistant Examiner*—Pedro Philogene
*Attorney, Agent, or Firm*—Cooley Godward LLP

[57] ABSTRACT

A device is described for containing abrasive particles expelled from air-abrasive apparati and permitting their removal. One embodiment disclosed is a device for containing abrasive material expelled by a gas abrasive dental apparatus. The device comprises a collecting chamber in fluid communication with a containment chamber. Between the two is a transfer opening for permitting passage of abrasive particles between them. The device contains an inlet that fluidly connects to the nozzle of an air-abrasive apparatus, and an outlet to permit contact of abrasive particles with the surface to be treated. Excess abrasive particles are collected into the collecting chamber and transferred by vacuum or pressure to the containment chamber. The containment chamber contains a porous member which entraps the particles while permitting gas to flow freely out of the device. The disclosure includes several embodiments of the device depending on the particular application. The disclosure includes a process for abrading a tooth service using the disclosed device.

45 Claims, 4 Drawing Sheets

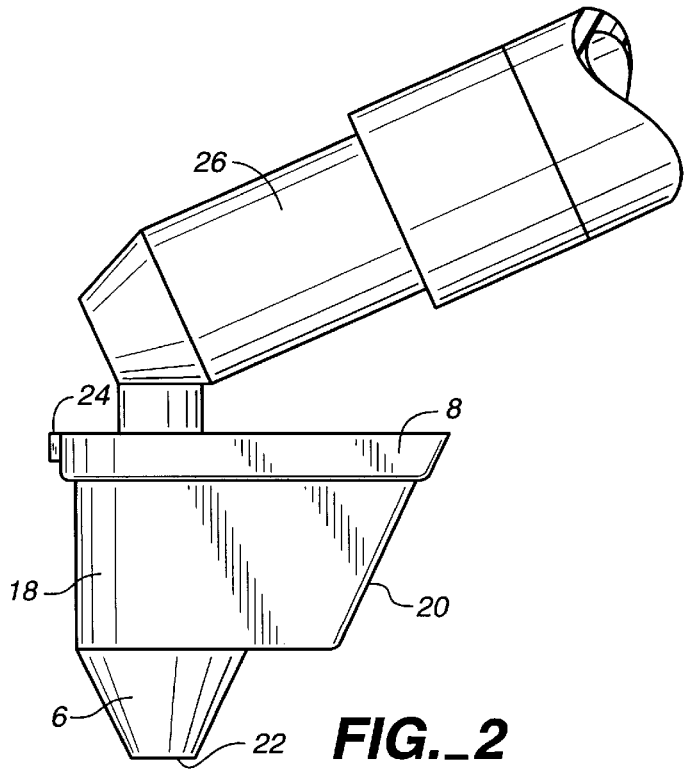
FIG._1
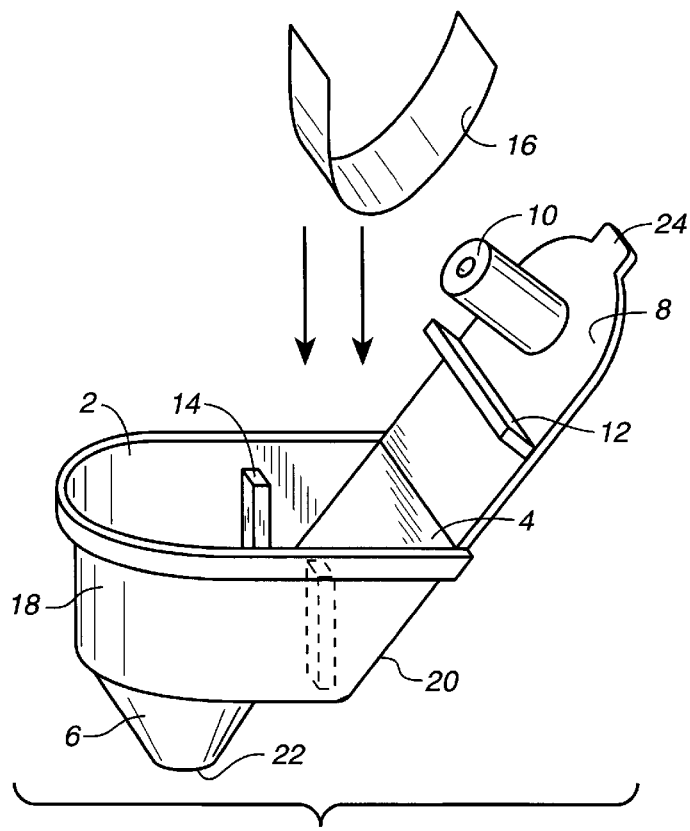
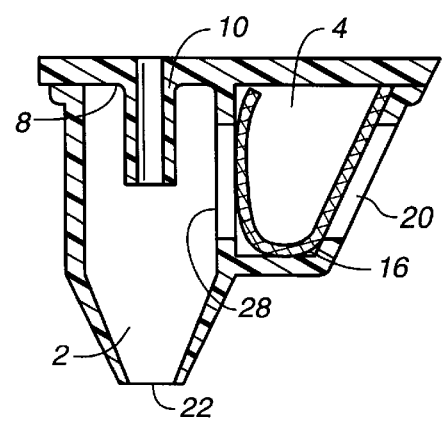
FIG._2          FIG._4

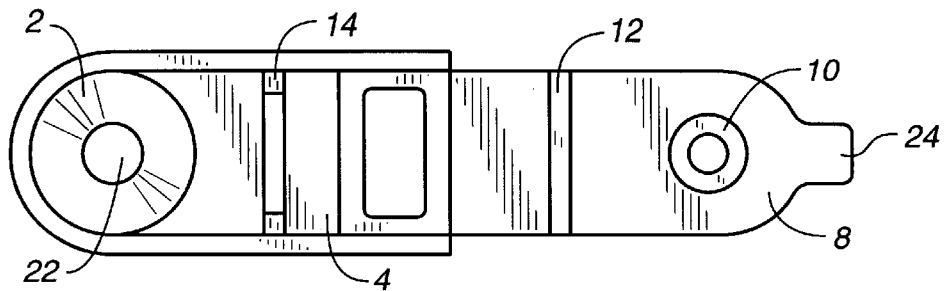
FIG._3
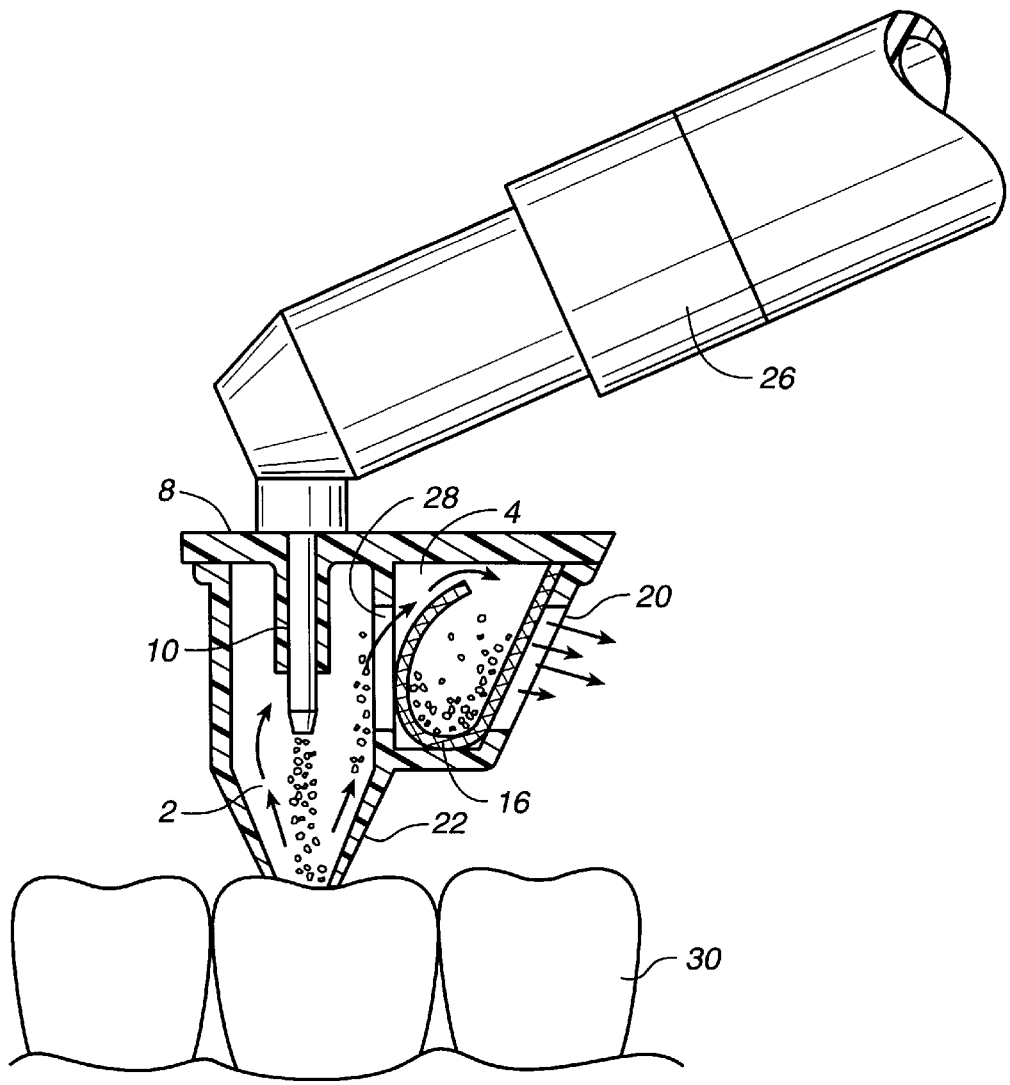
FIG._5

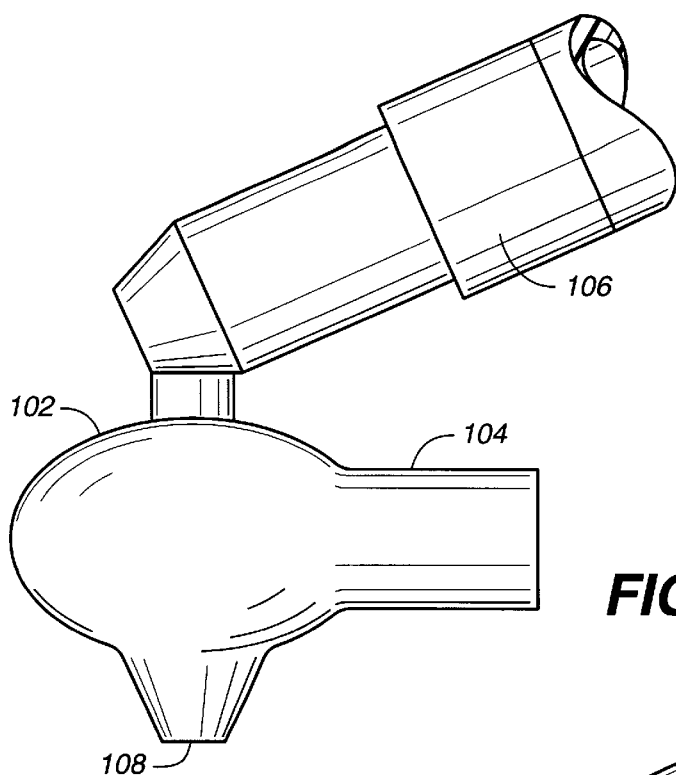
FIG._6
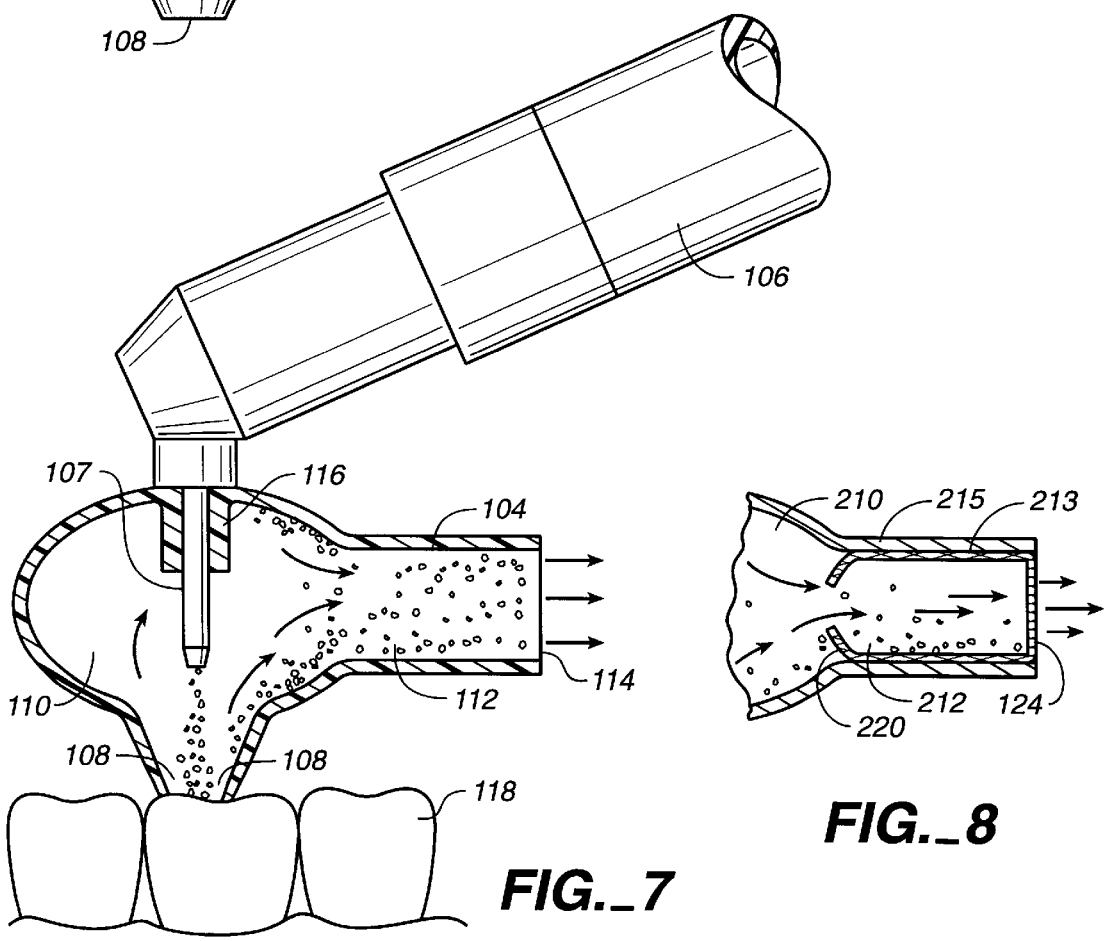
FIG._7
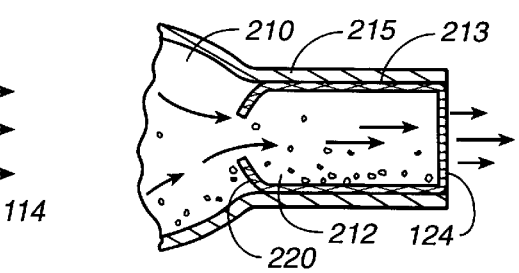
FIG._8

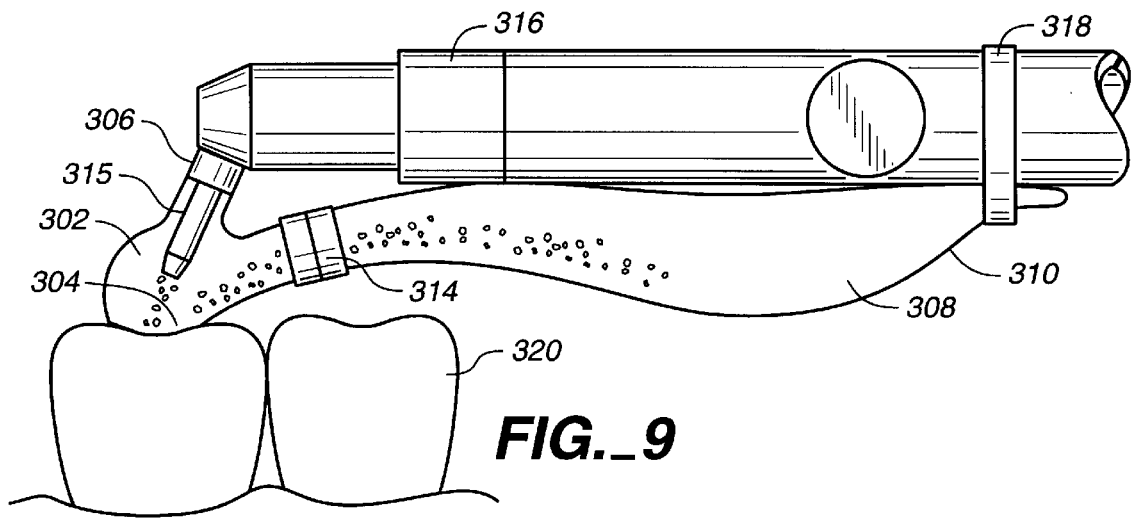
FIG._9
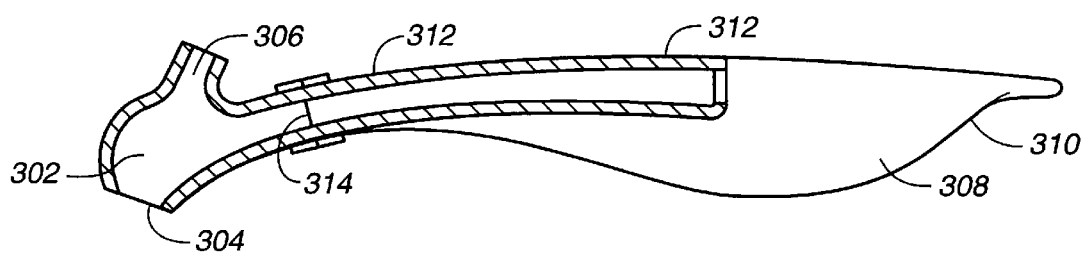
FIG._10

DEVICE FOR CONTAINING EXCESS ABRASIVE MATERIAL

BACKGROUND

1. Field of the invention

This invention relates to gas-abrasive devices, and more particularly to devices for containing excess abrasive materials expelled by the gas abrasive apparatus. The invention is particularly useful for dental applications.

2. Background of the Invention

The use of sandblasting devices to contact various surfaces has been known for some time. These devices are also known in the art as airbrasive or air-abrasive devices. Such devices vary in size and design depending on the particularly utility desired.

One area where use of these devices has proved advantageous is in the etching or abrading of small surfaces. Devices designed for this use are typically hand-held and capable of delivering fine streams of air-abrasive material through narrow nozzles.

A number of decades ago the use of air-abrasive devices gained favor in the dental art. The methods developed were termed "airbrasive techniques" and were designed to supplement the use of traditional dental drills to prepare a tooth for cavity repair, prophylaxis or other methods that required that a portion of the tooth be removed or that required the roughing of a tooth surface. The advantage of using air-abrasive techniques is that the dental patient experiences less trauma to the oral cavity due to the absence of perceptible pressure, vibration, noises created by the contact of a drill to tooth enamel, and heat created by frictional forces. This has resulted in reduced pain, apprehension, and fear by patients.

One disadvantage of the use of air-abrasive dental apparatus is that abrasive material are dispersed into the oral cavity during use in a relatively uncontrolled fashion, can be inhaled by the patient, and are difficult to remove after a procedure is complete. Another disadvantage is that such particles can be dispersed into the air and create a hygiene problem. Abrasive particles can carry pathogens and blood particles from the mouth and permit those pathogens and blood particles to contact otherwise uncontaminated surfaces.

Somewhat similar disadvantages exist with use of air-abrasive devices in other applications. Often it is desirable to prevent abrasive materials from contacting surfaces proximate to the target surface, from accumulating abrasive material on the target surface area, or from permitting fine abrasive particles from becoming airborne.

Several devices have been developed to affect the dispersion of abrasive particles within the oral cavity. Coston, U.S. Pat. No. 5,197,876 discloses a splatter guard for air polishing dental devices. The guard comprises a bell-shaped flexible cone that is attached to the end of an air abrasive device and guides abrasive particles towards the surface being treated. Ho, U.S. Pat. No. 5,356,292 discloses a dental sandblasting confiner in the form of a flexible transparent cup. The nozzle of a sandblasting device can be inserted in large opening of the cup which forms a mold around the nozzle. The Ho device contains additional openings for access to a tooth surface and for discharging output. Lokken, U.S. Pat. No. 4,611,992 discloses an anti-splash device that can be attached to a dental tool. The device comprises an inverted U-shaped member with legs for attaching the device to the dental tool. Wright, U.S. Pat. No. 4,850,868 discloses a spray shield comprising a modified tube that can be attached to the end of a dental handpiece. The device is used to direct material dispensed form the handpiece in a controlled fashion so as to minimize the amount of airborne particles.

While the above cited inventions address one or more of the described disadvantages of air abrasive systems, they are subject to several detrimental limitations. Although minimizing the amount of abrasive material released, by guiding it downward for instance, has certain benefits, it is more preferable to contain a substantial portion of released abrasive material and permit facile removal. Many of the devices in the prior art guide, but do not completely contain abrasive material nor permit easy removal thereof. Other devices that do permit removal of abrasive material are obtrusive and interfere with visualization of the surface to be abraded, making it difficult to perform precise dental procedures. Furthermore, those devices that do permit removal of abrasive material typically rely on a vacuum source to remove that material. Such a vacuum source adds additional expense and can also be intrusive.

Thus, there is a need for a device that can contain a substantial portion of the abrasive material expelled from a air-abrasive device while not obstructing visualization of the surface to be abraded and permitting removal of the abrasive material without the aid of a vacuum source.

OBJECTS OF THE INVENTION

One object of the present invention is to provide a device for containing abrasive material expelled by a gas abrasive apparatus.

Another object of the present invention is to provide a device for containing abrasive material expelled by a gas abrasive apparatus that is capable of containing a substantial portion of expelled abrasive material for easy removal.

Still another object of the present invention is to provide for a method to abrade a surface while containing abrasive material expelled from a gas apparatus.

Still another object of the present invention is to provide a process for making a device for containing material expelled by a gas abrasive apparatus.

Other objects may be apparent by one of ordinary skill upon reading the following specification and claims.

SUMMARY OF THE INVENTION

One aspect of this invention is a device for containing excess abrasive material expelled by a gas abrasive apparatus. The device comprises a collecting chamber for collecting abrasive particles, an inlet to the collecting chamber positioned to receive a nozzle of the apparatus, an outlet to the collecting chamber positioned to permit the exit of abrasive particles delivered by the apparatus to a surface, a containment chamber for containing abrasive particles, which containment chamber is in fluid communication with the collecting chamber, a transfer opening positioned between the collecting chamber and the containment chamber for permitting passage of abrasive particles from the collecting chamber to the containment chamber, a gas flow outlet from the containment chamber, a filtering means associated with the outlet from the containment chamber for retaining abrasive particles within the containment chamber while permitting the gas to exit the containment chamber.

Another aspect of the present invention is the combination of a gas abrasive apparatus and a device for containing excess abrasive material expelled by the apparatus which device comprises a collecting chamber for collecting abrasive particles, an inlet to the collecting chamber positioned to receive a nozzle of the apparatus, an outlet to the collecting chamber positioned to permit the exit of abrasive particles delivered by the apparatus to a surface, a containment chamber for containing abrasive particles, which containment chamber is in fluid communication with the collecting chamber, a transfer opening positioned between the collecting chamber and the containment chamber for permitting passage of abrasive particles from the collecting chamber to the containment chamber, a gas flow outlet from the containment chamber, a filtering means associated with the outlet from the containment chamber for retaining abrasive particles within the containment chamber while permitting the gas to exit the containment chamber.

Still another aspect of the present invention is process for abrading a tooth surface and containing abrasive material. The process comprises abrading the tooth surface with a gas abrasive dental apparatus in combination with a device for containing abrasive material expelled by the device.

BRIEF DESCRIPTION OF THE DRAWINGS

FIG. 1 is a perspective view of a preferred embodiment of the device of the present invention showing the collecting and containment chambers, a filtering means which also functions as a valve to prevent backflow, and a covering means pivotally connected to the device.

FIG. 2 is a side view of a preferred embodiment of the device of the present invention showing cooperation with a dental air-abrasive handpiece.

FIG. 3 is a is a top view of a preferred embodiment of the device of the present invention with the covering means open.

FIG. 4 is a cross-sectional view of a preferred embodiment of the device of the present invention showing various aspects of the collecting and containment chambers.

FIG. 5 shows a process for abrading a tooth surface a cross-sectional view of a preferred embodiment of the device of the present invention in use showing the flow of abrasive particles from a dental handpiece into the collecting chamber, contacting the tooth, and moving into the confinement chamber, which permits air to escape while the abrasive particles are entrapped.

FIG. 6 is a side view of second preferred embodiment of the device of the present invention showing cooperation with an air-abrasive handpiece.

FIG. 7 shows a process for abrading a tooth surface and a cross-sectional view of second preferred embodiment of the device of the present invention in use showing ejection of air-abrasive particles from the nozzle of an air-abrasive handpiece and their collection, subsequent to contact with a tooth surface, and entry into a confinement chamber where they are drawn into a tube by a vacuum.

FIG. 8 is a cross-sectional view of a third preferred embodiment of the device of the present invention showing a check valve between the collecting and containment chambers to prevent backflow of abrasive particles and also showing a filtering means located on the confinement chamber to entrap particles while permitting air to exit.

FIG. 9 shows a process for abrading a tooth surface and a transparent side view of a fourth preferred embodiment of the device of the present invention in use showing flow of abrasive particles from the collecting chamber and into a flexible confinement chamber after contact with a tooth surface.

FIG. 10 is a cross-sectional view of a fourth preferred embodiment of the device of the present invention showing the rigid portion of the collecting chamber and the flexible portion of the confinement chamber.

DETAILED DESCRIPTION OF THE PREFERRED EMBODIMENTS

One aspect of this invention is a device for containing abrasive material expelled by a gas abrasive apparatus. The device comprises a collecting chamber for collecting abrasive particles; an inlet to the collecting chamber positioned to receive a nozzle of the apparatus; an outlet to the collecting chamber positioned to permit the exit of abrasive particles delivered by the apparatus to a surface; a containment chamber for containing abrasive particles, which containment chamber is in fluid communication with the collecting chamber; a transfer opening positioned between the collecting chamber and the containment chamber for permitting passage of abrasive particles from the collecting chamber to the containment chamber; a gas flow outlet from the containment chamber; a filtering means associated with the outlet from the containment chamber for retaining abrasive particles within the containment chamber while permitting the gas to exit the containment chamber.

FIGS. 1–4 show different views of a preferred embodiment of the device of the present invention. Generally the device comprises a rigid or flexible body containing two chambers with a covering means connected pivotally thereto. The body comprises an outer wall 18 which is curved at one end elongated along the sides and connects to an angled wall 20 comprising the gas flow outlet. The curved portion of the outer wall 18 forms the collecting chamber 2. At the base of the collecting chamber 2 is a conical member 6 with the outlet 22 located at the tip of the cone. A transfer opening 14 separates the collecting chamber from a confinement chamber 4 via two vertically positioned ledges. The confinement chamber 4 is formed by a portion of the sides of the outer wall 18 and the angled wall 20. The angled wall 20 can comprise the filtering means or be cooperatively attached thereto, but will generally contain some opening to permit the exit of air or gas from the confinement chamber. In one preferred embodiment of the invention a flexible filtering means comprises a flexible sheet 16 of a porous material, such as paper or a polymer mesh. The dimensions of the flexible sheet 16 will be such that one end can cover an opening on the angled wall 20 to serve as the filtering means while the other end will fully or partially cover the transfer opening 14 so as to function as a valve to prevent backflow. A covering means 8 is pivotally (or hingedly) connected to one end of the angled wall 20 as shown in FIG. 1. Attached to the covering means is a ledge 12 to form part of the transfer opening 14, the nozzle inlet 10, and a protruding member 24 to help facilitate opening and closing of the covering means 8. The inlet 10 comprises a bored cylinder for snugly receiving the nozzle of an air-abrasive handpiece.

The dimensions of the device of the present invention will vary depending on the particular application. Generally the device will be of a size that will enable it to be slidingly attached to the nozzle of gas-abrasive apparatus 26 via the inlet 10 and permit the combination to be inserted into the oral cavity of a patient for use. The diameter of the outlet 22 should be such as to permit sufficient exposure of the tooth surface to enable abrasive material to adequately abrade the surface. Similarly, the materials used to construct the device of the present invention will vary depending on the application. The device could be rigid or flexible, opaque or transparent and can comprise such materials as polyethylene, polypropylene, and polyurethane. Preferably the material will be polyethylene.

FIG. 5 shows a process for abrading a tooth surface and containing abrasive material, which process comprises abrading the tooth surface with a gas abrasive dental apparatus in combination with a device for containing abrasive material expelled by the device.

Generally, the nozzle of an air-abrasive dental apparatus 26 will be slidingly inserted into the opening 10 of the device as shown in FIG. 5. The outlet 22 of the device will be snugly placed on the tooth surface and the abrasive material will be expelled from the air-abrasive apparatus to abrade the tooth surface. Abrasive material will then be deflected back from the tooth surface and guided by the collecting chamber 2 to the transfer opening 14 and into the confinement chamber 4 as shown in FIG. 5. Abrasive particles will become entrapped in the confinement chamber 4 by the filtering means 16, which will also prevent a backflow of the abrasive particles through the transfer opening 14. Air or gas will pass through the angled wall 20 with minimal resistance.

FIGS. 6–7 shows a second preferred embodiment of the device of the present invention. In this preferred embodiment, the collecting chamber 110 comprises a curved member 102 with an inlet 116 comprising a bored shaft and an outlet 108 at the tip of a conical member opposite the inlet 116. The confinement chamber 112 comprises a cylinder 104 attached to the containment chamber 110. The gas flow outlet 114 is located at the end of the confinement chamber 112 and can be connected to a vacuum source to draw abrasive material out of the collecting chamber and into and out of the confinement chamber.

FIG. 7 shows a process for abrading a tooth surface using the second preferred embodiment of the device of the present invention. The nozzle 107 of a hand-held air-abrasive dental apparatus 106 is slidingly inserted into the inlet 116. Abrasive material is expelled from the nozzle on to the tooth surface 118 through the outlet 108. A vacuum line may be attached to the end of the confinement chamber 112 to draw abrasive material out of the collecting chamber 110 so that it may be entrapped in the confinement chamber 112 as air flows through the filtering means 114. FIG. 8 shows an alternative embodiment where a check-valve 220 prevents blackflow of abrasive material from the confinement chamber 212 to the collecting chamber 210. Here the inner wall 213 slidably fits into the outer wall 215 and can be removed when full of abrasive material.

FIG. 9 is a perspective view of a method for abrading a tooth surface, and FIG. 10 is a crossectional view of a third preferred embodiment of the device of the present invention. In this embodiment the nozzle 315 of a hand-held air-abrasive dental apparatus 316 is slidingly inserted into an inlet 306. The end of a ergonomically curved confinement chamber 308 is attached to a clamp 318 located on the shaft of the dental apparatus 316 to secure it in place. Abrasive material is expelled from the nozzle and contacts the surface of a tooth 320 through an outlet 304. Abrasive material then is collected into the collecting chamber 302 and forced by the gas pressures created by the nozzle of the dental apparatus 316 into the confinement chamber 308 through a transition opening 314. The confinement chamber 308 comprises a flexible porous material, such as paper or polymer mesh and also comprises the filtering means 308. Abrasive material is contained in the containment chamber 308 while gas or air can escape via the filtering means 310. A support wall frame 312 extends from the collecting chamber 302 to the confinement chamber for increased support of the flexible confinement chamber 308.

The dimensions of these preferred embodiments will also depend on the application, but will be such as to minimize obstruction while maximizing ease of use. Similarly, the materials will vary depending on the application. Such applications include non-dental applications and may also require different materials of manufacture for the various embodiments.

Having completed the description of the apparatus in both its broad aspects and preferred embodiments, one of ordinary skill in the art may identify other aspects and embodiments of the invention that would be apparent and obvious to one upon reading the specification. Such aspects of the invention are meant to be included within the scope of this disclosure and claims.

The subject matter claimed is:

1. A device for containing excess abrasive material expelled by a gas abrasive apparatus, which device comprises a collecting chamber for collecting abrasive particles, an inlet to the collecting chamber positioned to receive a nozzle of the apparatus, an outlet to the collecting chamber positioned to permit the exit of abrasive particles delivered by the apparatus to a surface, a containment chamber for containing abrasive particles, which containment chamber is in fluid communication with the collecting chamber, a transfer opening positioned between the collecting chamber and the containment chamber for permitting passage of abrasive particles from the collecting chamber to the containment chamber, a gas flow outlet from the containment chamber, a filtering means associated with the gas flow outlet from the containment chamber for retaining abrasive particles within the containment chamber while permitting the gas to exit the containment chamber.

2. The device of claim 1, wherein the device is for use with a dental gas abrasive apparatus.

3. The device of claim 1, wherein a covering means is pivotally connected to the device to permit removal of contained abrasive particles.

4. The device of claim 3, wherein the inlet to the collecting chamber is positioned on the covering means and a conduit for slidingly receiving the nozzle of the dental apparatus is connected to the inlet.

5. The device of claim 1, wherein the filtering means comprises a porous membrane.

6. The device of claim 1, wherein the filtering means is removable.

7. The device of claim 1, wherein the filtering means is integral with the outlet from the containment chamber.

8. The device of claim 1, wherein a suction means is connected cooperatively to the gas flow outlet.

9. The device of claim 1, wherein the filtering means comprises a removable flexible porous membrane.

10. The device of claim 9, wherein a portion of the porous membrane covers the containment chamber side of the transfer opening and functions as a valve to prevent backflow of abrasive material from the containment chamber to the collecting chamber.

11. The device of claim 1, wherein the transfer opening contains a valve for preventing backflow of abrasive material from the containment chamber to the collecting chamber.

12. The device of claim 1, wherein the containment chamber is a flexible bag.

13. The device of claim 12, wherein the flexible bag is removable.

14. The device of claim 13, wherein the flexible bag is porous.

15. The device of claim 14, wherein the flexible bag functions as the filtering means.

16. A combination of a gas abrasive apparatus and a device for containing excess abrasive material expelled by the apparatus, which combination comprises a gas abrasive handpiece for having a nozzle and a source of a pressurized gas abrasive stream directed to the nozzle, a collecting chamber for collecting abrasive particles, an inlet to the collecting chamber positioned to receive the nozzle of the apparatus, an outlet to the collecting chamber positioned to permit the exit of abrasive particles delivered by the nozzle to a surface, a containment chamber for containing abrasive particles, which containment chamber is in fluid communication with the collecting chamber, a transfer opening positioned between the collecting chamber and the containment chamber for permitting passage of abrasive particles from the collecting chamber to the containment chamber, a gas flow outlet from the containment chamber, a filtering means associated with the outlet from the containment chamber for retaining abrasive particles within the containment chamber while permitting the gas to exit the containment chamber.

17. The combination of claim 16, wherein the combination is for use for treating tooth surfaces.

18. The combination of claim 16, wherein a covering means is pivotally connected to the device to permit removal of contained abrasive particles.

19. The combination of claim 18, wherein the nozzle inlet to the collecting chamber is positioned on the covering means and a conduit for slidingly receiving the nozzle of the dental apparatus is connected to the inlet.

20. The combination of claim 16, wherein the filtering means comprises a porous membrane.

21. The device of claim 16, wherein the filtering means is removable.

22. The combination of claim 16, wherein the filtering means is integral with the outlet from the containment chamber.

23. The combination of claim 16, wherein a suction means is connected cooperatively to the gas flow outlet.

24. The combination of claim 16, wherein the filtering means comprises a removable flexible porous membrane.

25. The combination of claim 24, wherein a portion of the membrane covers the containment chamber side of the transfer opening and functions as a valve to prevent backflow of abrasive material from the containment chamber to the collecting chamber.

26. The combination of claim 16, wherein the transfer opening contains a valve for preventing backflow of abrasive material from the containment chamber to the collecting chamber.

27. The combination of claim 16, wherein the containment chamber is a flexible bag.

28. The combination of claim 27, wherein the flexible bag is removable.

29. The combination of claim 28, wherein the flexible bag is porous.

30. The combination of claim 29, wherein the flexible bag functions as the filtering means.

31. A process for abrading a tooth surface and containing abrasive material, which process comprises abrading the tooth surface with a gas abrasive dental apparatus in combination with a device for containing abrasive material expelled by the device, which device comprises a collecting chamber for collecting abrasive particles, an inlet to the collecting chamber positioned to receive a nozzle of the apparatus, an outlet to the collecting chamber positioned to permit the exit of abrasive particles delivered by the apparatus to a surface, a containment chamber for containing abrasive particles, which containment chamber is in fluid communication with the collecting chamber, a transfer opening positioned between the collecting chamber and the containment chamber for permitting passage of abrasive particles from the collecting chamber to the containment chamber, a gas flow outlet from the containment chamber, a filtering means associated with the gas flow outlet from the containment chamber for retaining abrasive particles within the containment chamber while permitting the gas to exit the containment chamber.

32. The process of claim 31, wherein the device is for use with a dental gas abrasive apparatus.

33. The process of claim 31, wherein a covering means is pivotally connected to the device to permit removal of contained abrasive particles.

34. The process of claim 33, wherein the inlet to the collecting chamber is positioned on the covering means and a conduit for slidingly receiving the nozzle of the dental apparatus is connected to the inlet.

35. The process of claim 31, wherein the filtering means comprises a porous membrane.

36. The process of claim 31, wherein the filtering means is removable.

37. The process of claim 31, wherein the filtering means is integral with the outlet from the containment chamber.

38. The process of claim 31, wherein a suction means is connected cooperatively to the gas flow outlet.

39. The process of claim 31, wherein the filtering means comprises a removable flexible porous membrane.

40. The process of claim 39, wherein a portion of the porous membrane covers the containment chamber side of the transfer opening and functions as a valve to prevent backflow of abrasive material from the containment chamber to the collecting chamber.

41. The process of claim 31, wherein the transfer opening contains a valve for preventing backflow of abrasive material from the containment chamber to the collecting chamber.

42. The process of claim 31, wherein the containment chamber is a flexible bag.

43. The process of claim 42, wherein the flexible bag is removable.

44. The process of claim 43, wherein the flexible bag is porous.

45. The process of claim 44, wherein the flexible bag functions as the filtering means.

* * * * *